(12) United States Patent
Hashimoto et al.

(10) Patent No.: US 12,298,269 B2
(45) Date of Patent: May 13, 2025

(54) SENSOR ELEMENT AND GAS SENSOR

(71) Applicant: NGK INSULATORS, LTD., Aichi (JP)

(72) Inventors: Satoru Hashimoto, Chiryu (JP);
Shingo Sokawa, Okazaki (JP);
Yoshihiko Yamamura, Nagoya (JP);
Kosuke Ujihara, Obu (JP)

(73) Assignee: NGK INSULATORS, LTD., Nagoya (JP)

(*) Notice: Subject to any disclaimer, the term of this patent is extended or adjusted under 35 U.S.C. 154(b) by 466 days.

(21) Appl. No.: 17/887,540

(22) Filed: Aug. 15, 2022

(65) Prior Publication Data
US 2023/0071139 A1  Mar. 9, 2023

(30) Foreign Application Priority Data

Aug. 25, 2021 (JP) .................. 2021-137151
Aug. 5, 2022 (JP) .................. 2022-125362

(51) Int. Cl.
| | |
|---|---|
| *G01N 27/407* | (2006.01) |
| *G01N 27/406* | (2006.01) |
| *G01N 27/41* | (2006.01) |
| *G01N 33/00* | (2006.01) |

(52) U.S. Cl.
CPC ..... *G01N 27/4071* (2013.01); *G01N 27/4067* (2013.01); *G01N 27/41* (2013.01); *G01N 33/0037* (2013.01)

(58) Field of Classification Search
None
See application file for complete search history.

(56) References Cited

U.S. PATENT DOCUMENTS

2017/0052143 A1   2/2017   Watanabe et al.

FOREIGN PATENT DOCUMENTS

JP   2017-041431 A   2/2017

*Primary Examiner* — J. Christopher Ball
(74) *Attorney, Agent, or Firm* — MATTINGLY & MALUR, PC

(57) ABSTRACT

A sensor element includes an element body that contains a measurement-object gas flow section and a heat generation portion. The measurement-object gas flow section includes a main pump chamber, an auxiliary pump chamber, and a measurement chamber. A distance X1 in a left-right direction between a part of a first inner linear portion and a part of a second inner linear portion of the heat generation portion that overlap a main pump chamber projection region is equal to or more than $\frac{1}{3}$ of a width Wp of the main pump chamber projection region in the left-right direction. A distance X2 in the left-right direction between a part of the first inner linear portion and a part of the second inner linear portion that overlap an auxiliary pump chamber projection region is equal to or more than 0.4 times the width Wp.

4 Claims, 5 Drawing Sheets

SENSOR ELEMENT AND GAS SENSOR

CROSS-REFERENCE TO RELATED APPLICATION

The present application claims priority from Japanese Patent Application No. 2021-137151, filed on Aug. 25, 2021, and Japanese Patent Application No. 2022-125362, filed on Aug. 5, 2022, the entire contents of which are incorporated herein by reference.

BACKGROUND OF THE INVENTION

1. Field of the Invention

The present invention relates to a sensor element and a gas sensor.

2. Description of the Related Art

A known sensor element is used for a gas sensor that detects a specific gas concentration such as a NOx concentration in measurement-object gas such as exhaust gas of an automobile. PTL 1, for example, discloses a sensor element that includes a layered body of oxygen-ion-conductive solid electrolyte layers, an internal cavity that is formed in the layered body, a pump cell that pumps into and pumps out oxygen in the internal cavity, and a measurement electrode that is disposed in the layered body. In the case where the NOx concentration is detected by using the element, the oxygen concentration of the measurement-object gas in the internal cavity is first adjusted. Subsequently, NOx in the measurement-object gas after the oxygen concentration is adjusted is reduced around the measurement electrode. The NOx concentration in the measurement-object gas is detected based on a pump current that flows when oxygen around the measurement electrode is pumped out. The sensor element in PTL 1 includes a heating element that serves a temperature adjustment function of heating the sensor element and keeping temperature in order to increase the oxygen-ion-conductivity of a solid electrolyte. The heating element includes a linear portion and a bend portion. The resistance value of the bend portion per unit length is lower than that of the linear portion at least at a temperature in a temperature range of no less than 700° C. and no more than 900° C. Consequently, the temperature of the bend portion that is more likely to deteriorate than the linear portion is unlikely to increase, and the bend portion can be inhibited from deteriorating.

CITATION LIST

Patent Literature

PTL 1: JP 2017-041431 A

SUMMARY OF THE INVENTION

In some cases, a stress is applied to the vicinity of the internal cavity of the sensor element when the heating element heats the sensor element. In some cases, the sensor element cracks due to the stress. Consequently, there is a need to reduce the stress. In PTL 1, the stress that is applied to the vicinity of the internal cavity is not considered.

The present invention has been accomplished to solve the problem, and it is a main object of the present invention to reduce a stress that is applied to the vicinity of an internal cavity of a sensor element when the heating element generates heat.

The present invention takes a measure described below to achieve the main object described above.

[1] A sensor element according to the present invention includes an element body that includes an oxygen-ion-conductive solid electrolyte layer, that contains a measurement-object gas flow section into which measurement-object gas is introduced and through which the measurement-object gas flows, that has a longitudinal direction, a transverse direction, and a thickness direction perpendicular to the longitudinal direction and the transverse direction, and that has a plate shape, a main pump cell that adjusts an oxygen concentration of a main pump chamber in the measurement-object gas flow section, an auxiliary pump cell that adjusts an oxygen concentration of an auxiliary pump chamber that is formed downstream of the main pump chamber in the measurement-object gas flow section, a measurement pump cell that adjusts an oxygen concentration of a measurement chamber that is formed downstream of the auxiliary pump chamber in the measurement-object gas flow section, and a heating element that heats the element body. The heating element includes a first outer linear portion and a second outer linear portion that are arranged in the transverse direction and that have a length direction parallel with the longitudinal direction, a first inner linear portion and a second inner linear portion that are disposed between the first outer linear portion and the second outer linear portion in the transverse direction and that have a length direction parallel with the longitudinal direction, a first bend portion that connects the first outer linear portion and the first inner linear portion to each other at a first end in the longitudinal direction, a second bend portion that connects the first inner linear portion and the second inner linear portion to each other at a second end in the longitudinal direction, and a third bend portion that connects the second inner linear portion and the second outer linear portion to each other at the first end in the longitudinal direction. At least a part of the first inner linear portion and a part of the second inner linear portion overlap a main pump chamber projection region on which the main pump chamber is projected toward the heating element in the thickness direction, and at least a part of the first inner linear portion and a part of the second inner linear portion overlap an auxiliary pump chamber projection region on which the auxiliary pump chamber is projected toward the heating element in the thickness direction. A distance X1 in the transverse direction between the part of the first inner linear portion and the part of the second inner linear portion that overlap the main pump chamber projection region is equal to or more than ⅓ of a width Wp of the main pump chamber projection region in the transverse direction. A distance X2 in the transverse direction between the part of the first inner linear portion and the part of the second inner linear portion that overlap the auxiliary pump chamber projection region is equal to or more than 0.4 times the width Wp.

As for the sensor element, positional relationships between the heating element and internal cavities (the main pump chamber, the auxiliary pump chamber, and the measurement chamber) of the sensor element satisfy conditions that the distance X1 is equal to or more than ⅓ of the width Wp, and the distance X2 is equal to or more than 0.4 times the width Wp. The distance X1 is a distance in the transverse direction between the part of the first inner linear portion and the part of the second inner linear portion of the heating element that overlap the main pump chamber projection region on which the main pump chamber is projected toward the heating element in the thickness direction. The distance X2 is a distance in the transverse direction between the part of the first inner linear portion and the part of the second inner linear portion of the heating element that overlap the auxiliary pump chamber projection region on which the auxiliary pump chamber is projected toward the heating element in the thickness direction. The width Wp corresponds to the length of the main pump chamber projection region in the transverse direction. When the conditions described above are satisfied, a stress that is applied to the vicinity of the internal cavities (the main pump chamber, the auxiliary pump chamber, and the measurement chamber) can be reduced when the heating element generates heat.

[2] As for the sensor element (the sensor element in [1] described above), the distance X1 may be more than 0.4 times the width Wp. This enables the effect of reducing the stress described above can be enhanced.

As for the sensor element (the sensor element in [1] or [2] described above), a unit resistance value ratio R3/R1 may be less than 1 at least at a temperature in a temperature range of no less than 700° C. and no more than 900° C., where a unit resistance value R1 [μΩ/mm] is a resistance value per unit length of a pump chamber overlapping portion that overlaps a pump chamber projection region on which the main pump chamber and the auxiliary pump chamber are projected toward the heating element in the thickness direction in the heating element, and a unit resistance value R3 [μΩ/mm] is a resistance value per unit length of a measurement chamber overlapping portion that overlaps a measurement chamber projection region on which the measurement chamber is projected toward the heating element in the thickness direction in the heating element. When the unit resistance value R3 is too large, a difference between temperature in the vicinity of the main pump chamber and the auxiliary pump chamber and temperature in the vicinity of the measurement chamber is too small, and the precision of detection of a specific gas concentration decreases in some cases. When the unit resistance value ratio R3/R1 is less than 1, the precision of detection can be inhibited from decreasing.

In this case, the measurement chamber overlapping portion may be at least a part of the second bend portion. In other words, as for the heating element, the second bend portion may overlap the measurement chamber projection region.

[4] A gas sensor according to the present invention includes the sensor element in any one of [1] to [3] described above. For this reason, the gas sensor achieves the same effects as the sensor element according to the present invention described above such as the effect of reducing the stress that is applied to the vicinity of the internal cavities of the sensor element when the heating element generates heat.

DETAILED DESCRIPTION OF THE INVENTION

Figure 1:
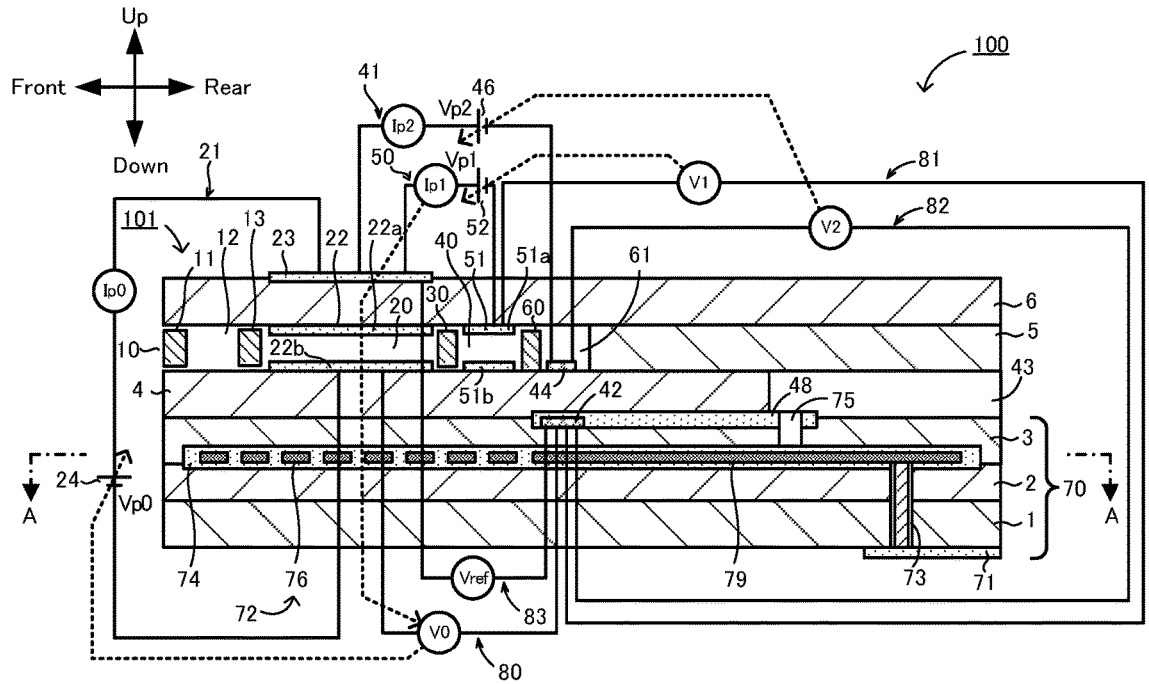
FIG. 1 is a schematic sectional view of an example of the structure of a gas sensor 100.
Figure 2:
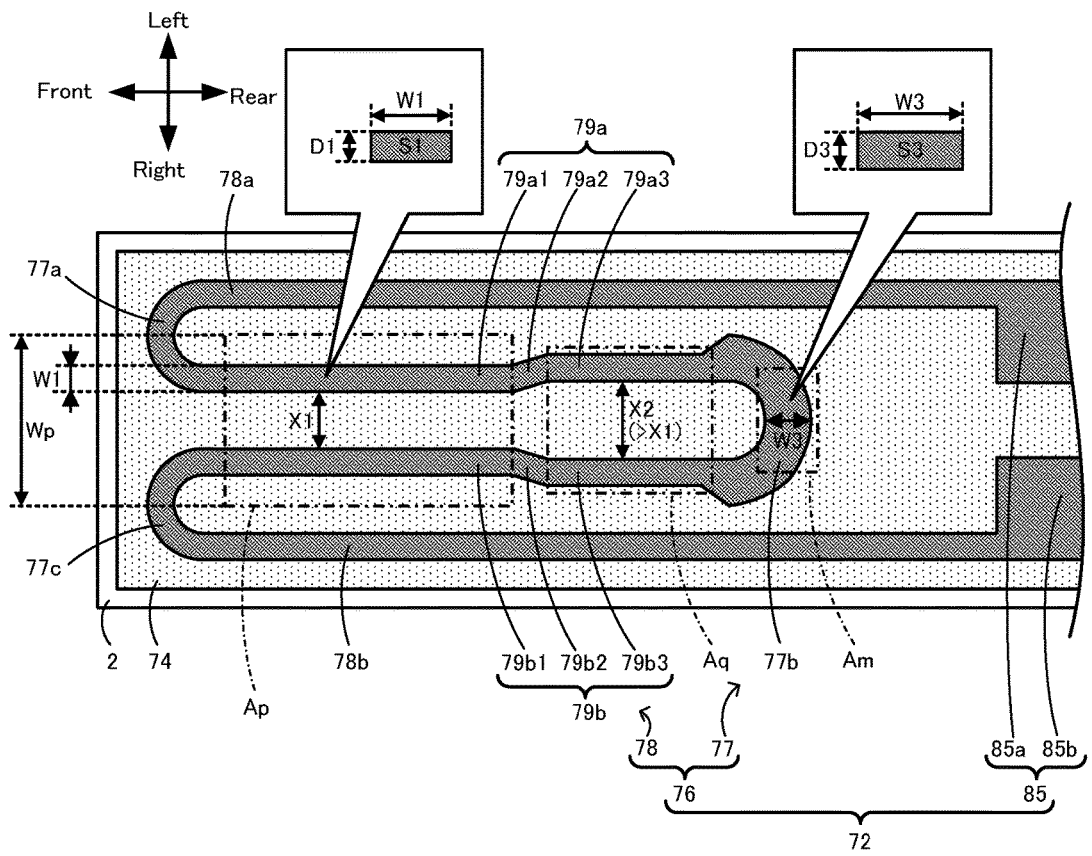
FIG. 2 is a sectional view of FIG. 1 taken along line A-A.

An embodiment of the present invention will now be described with reference to the drawings. FIG. 1 is a schematic sectional view of an example of the structure of a gas sensor 100 according to an embodiment of the present invention. FIG. 2 is a sectional view of FIG. 1 taken along line A-A. The gas sensor 100 detects a specific gas concentration such as a NOx concentration in measurement-object gas such as exhaust gas of an automobile by using a sensor element 101. The sensor element 101 has an elongate rectangular parallelepiped shape. The longitudinal direction of the sensor element 101 (a left-right direction in FIG. 1) is referred to as a front-rear direction, and the thickness direction of the sensor element 101 (an up-down direction in FIG. 1) is referred to as an up-down direction. The width direction (a direction perpendicular to the front-rear direction and the up-down direction) of the sensor element 101 is referred to as a left-right direction.

The sensor element 101 has a layered body of six layers of a first substrate layer 1, a second substrate layer 2, a third substrate layer 3, a first solid electrolyte layer 4, a spacer layer 5, and a second solid electrolyte layer 6 that are composed of respective oxygen-ion-conductive solid electrolyte layers such as zirconia ($ZrO_2$) layers and that are stacked in this order from below in the figure. A solid electrolyte of which the six layers are composed is elaborate and airtight. The sensor element 101 is manufactured, for example, in a manner in which a predetermined process and circuit pattern printing, for example, are performed on ceramic green sheets that correspond to the respective layers, and the sheets are subsequently stacked and fired into an integrally formed piece.

At a position near a front end portion (near a left end portion in FIG. 1) of the sensor element 101 between a lower surface of the second solid electrolyte layer 6 and an upper surface of the first solid electrolyte layer 4, a gas inlet 10, a first diffusion control section 11, a buffer space 12, a second diffusion control section 13, a first internal cavity 20, a third diffusion control section 30, a second internal cavity 40, a fourth diffusion control section 60, and a third internal cavity 61 are formed so as to be adjacent to each other and so as to communicate with each other in this order.

The gas inlet 10, the buffer space 12, the first internal cavity 20, the second internal cavity 40, and the third internal cavity 61 are spaces in the sensor element 101 each of which is formed by hollowing the spacer layer 5 such that an upper part is defined by the lower surface of the second solid electrolyte layer 6, a lower part is defined by the upper surface of the first solid electrolyte layer 4, and a side part is defined by a side surface of the spacer layer 5.

Each of the first diffusion control section 11, the second diffusion control section 13, and the third diffusion control section 30 is formed as two slits that are long from side to side (the longitudinal direction of openings is a direction perpendicular to the figure). The fourth diffusion control section 60 is formed as a slit that is formed as a gap adjacent to the lower surface of the second solid electrolyte layer 6 and that is long from side to side (the longitudinal direction of openings is the direction perpendicular to the figure). A portion extending from the gas inlet 10 to the third internal cavity 61 is also referred to as a measurement-object gas flow section.

A reference gas introduction space 43 is formed at a position that is farther than the measurement-object gas flow section from an end and at a position at which a side part is defined by a side surface of the first solid electrolyte layer 4 between an upper surface of the third substrate layer 3 and a lower surface of the spacer layer 5. For example, air is introduced, as reference gas when the NOx concentration is measured, into the reference gas introduction space 43.

An air introduction layer 48 is a layer composed of porous ceramics, and the reference gas is introduced into the air introduction layer 48 via the reference gas introduction space 43. The air introduction layer 48 is formed so as to cover a reference electrode 42.

The reference electrode 42 is an electrode formed such that the electrode is interposed between the upper surface of the third substrate layer 3 and the first solid electrolyte layer 4, and the air introduction layer 48 in communication with the reference gas introduction space 43 is disposed therearound as described above. The use of the reference electrode 42 enables an oxygen concentration (an oxygen partial pressure) in the first internal cavity 20, the second internal cavity 40, and the third internal cavity 61 to be measured as described later. The reference electrode 42 is formed as a porous cermet electrode (for example, a cermet electrode composed of Pt and $ZrO_2$).

In the measurement-object gas flow section, the gas inlet 10 is a region opened to the exterior space, and the measurement-object gas is taken into the sensor element 101 from the exterior space via the gas inlet 10. The first diffusion control section 11 gives a predetermined diffusion resistance to the measurement-object gas that is taken in via the gas inlet 10. The buffer space 12 is formed to guide the measurement-object gas that is introduced via the first diffusion control section 11 toward the second diffusion control section 13. The second diffusion control section 13 gives a predetermined diffusion resistance to the measurement-object gas that is introduced into the first internal cavity 20 from the buffer space 12. When the measurement-object gas is introduced from a location outside the sensor element 101 into the first internal cavity 20, the measurement-object gas that is rapidly taken into the sensor element 101 via the gas inlet 10 as a result of variation in the pressure of the measurement-object gas in the exterior space (in the case where the measurement-object gas is exhaust gas of an automobile, pulsation of an exhaust pressure) is not directly introduced into the first internal cavity 20 but is introduced into the first internal cavity 20 after the variation in the pressure of the measurement-object gas is canceled out via the first diffusion control section 11, the buffer space 12, and the second diffusion control section 13. Consequently, the variation in the pressure of the measurement-object gas that is introduced into the first internal cavity 20 is almost negligible. The first internal cavity 20 is formed as a space used to adjust the oxygen partial pressure in the measurement-object gas that is introduced via the second diffusion control section 13. The oxygen partial pressure is adjusted by operation of a main pump cell 21.

The main pump cell 21 is an electrochemical pump cell that includes an inner pump electrode 22 that includes a ceiling electrode portion 22a that is disposed on substantially the entire region of the lower surface of the second solid electrolyte layer 6 that faces the first internal cavity 20, an outer pump electrode 23 that is disposed in a region of the upper surface of the second solid electrolyte layer 6 opposite the ceiling electrode portion 22a such that the outer pump electrode 23 is exposed to the exterior space, and the second solid electrolyte layer 6 that is interposed between these electrodes.

The inner pump electrode 22 is formed so as to extend over upper and lower solid electrolyte layers (the second solid electrolyte layer 6 and the first solid electrolyte layer 4) that define the first internal cavity 20 and the spacer layer 5 that defines side walls. Specifically, the ceiling electrode portion 22a is formed on the lower surface of the second solid electrolyte layer 6 that defines the ceiling surface of the first internal cavity 20, a bottom electrode portion 22b is formed on the upper surface of the first solid electrolyte layer 4 that defines the bottom surface thereof, side electrode portions (not illustrated) are formed on side wall surfaces (inner surfaces) of the spacer layer 5 that define both side wall portions of the first internal cavity 20 such that the ceiling electrode portion 22a and the bottom electrode portion 22b are connected to each other, and the side electrode portions are disposed such that a tunnel shaped structure is formed at positions at which the side electrode portions are disposed.

The inner pump electrode 22 and the outer pump electrode 23 are formed as porous cermet electrodes (for example, cermet electrodes composed of Pt containing 1% of Au and $ZrO_2$). The inner pump electrode 22 that comes into contact with the measurement-object gas is composed of a material that has impaired ability to reduce NOx components in the measurement-object gas.

In the main pump cell 21, a desired voltage Vp0 is applied between the inner pump electrode 22 and the outer pump electrode 23 to cause a pump current Ip0 to flow in a positive direction or in a negative direction between the inner pump electrode 22 and the outer pump electrode 23, and oxygen in the first internal cavity 20 can be consequently pumped out to the exterior space or oxygen in the exterior space can be consequently pumped into the first internal cavity 20.

In order to detect the oxygen concentration (the oxygen partial pressure) in the atmosphere in the first internal cavity 20, an electrochemical sensor cell, that is, a main pump controlling oxygen partial pressure detection sensor cell 80 includes the inner pump electrode 22, the second solid electrolyte layer 6, the spacer layer 5, the first solid electrolyte layer 4, the third substrate layer 3, and the reference electrode 42.

An electromotive force (a voltage V0) in the main pump controlling oxygen partial pressure detection sensor cell 80 is measured and the oxygen concentration (the oxygen partial pressure) in the first internal cavity 20 is consequently known. Feedback control on the voltage Vp0 of a variable power supply 24 is implemented such that the voltage V0 becomes a target value and the pump current Ip0 is consequently controlled. This enables the oxygen concentration in the first internal cavity 20 to be held at a predetermined constant value.

The third diffusion control section 30 gives a predetermined diffusion resistance to the measurement-object gas the oxygen concentration (the oxygen partial pressure) of which has been controlled by operation of the main pump cell 21 in the first internal cavity 20 and guides the measurement-object gas toward the second internal cavity 40.

The second internal cavity 40 is formed as a space in which an auxiliary pump cell 50 adjusts the oxygen partial pressure of the measurement-object gas that is introduced via the third diffusion control section 30 after the oxygen concentration (the oxygen partial pressure) is adjusted in the first internal cavity 20 in advance. This enables the oxygen concentration in the second internal cavity 40 to be kept constant with high precision, and the gas sensor 100 can consequently measure the NOx concentration with high precision.

The auxiliary pump cell 50 is an auxiliary electrochemical pump cell that includes an auxiliary pump electrode 51 that includes a ceiling electrode portion 51a that is disposed on substantially the entire region of the lower surface of the second solid electrolyte layer 6 that faces the second internal cavity 40, the outer pump electrode 23 (which is not limited to the outer pump electrode 23, and a proper electrode outside the sensor element 101 suffices), and the second solid electrolyte layer 6.

The auxiliary pump electrode 51 is disposed in the second internal cavity 40 at a tunnel shaped structure as in the inner pump electrode 22 that is disposed in the first internal cavity 20 described above. That is, the ceiling electrode portion 51a is formed on the second solid electrolyte layer 6 that defines the ceiling surface of the second internal cavity 40, a bottom electrode portion 51b is formed on the first solid electrolyte layer 4 that defines the bottom surface of the second internal cavity 40, and there is the tunnel shaped structure in which side electrode portions (not illustrated) that connect the ceiling electrode portion 51a and the bottom electrode portion 51b to each other are formed on both wall surfaces of the spacer layer 5 that defines side walls of the second internal cavity 40. The auxiliary pump electrode 51 is composed of a material that has impaired ability to reduce the NOx components in the measurement-object gas as in the inner pump electrode 22.

In the auxiliary pump cell 50, a desired voltage Vp1 is applied between the auxiliary pump electrode 51 and the outer pump electrode 23, and oxygen in the atmosphere in the second internal cavity 40 can be consequently pumped out to the exterior space or oxygen in the exterior space can be consequently pumped into the second internal cavity 40.

In order to control the oxygen partial pressure in the atmosphere in the second internal cavity 40, an electrochemical sensor cell, that is, an auxiliary pump controlling oxygen partial pressure detection sensor cell 81 includes the auxiliary pump electrode 51, the reference electrode 42, the second solid electrolyte layer 6, the spacer layer 5, the first solid electrolyte layer 4, and the third substrate layer 3.

Pumping of the auxiliary pump cell 50 is performed by using a variable power supply 52 the voltage of which is controlled based on an electromotive force (a voltage V1) that is detected by the auxiliary pump controlling oxygen partial pressure detection sensor cell 81. Consequently, the oxygen partial pressure in the atmosphere in the second internal cavity 40 is controlled to be a low partial pressure that does not substantially affect the measurement of NOx.

In addition to this, a pump current Ip1 thereof is used for control of the electromotive force of the main pump controlling oxygen partial pressure detection sensor cell 80. Specifically, the pump current Ip1 is inputted, as a control signal, into the main pump controlling oxygen partial pressure detection sensor cell 80, and the target value of the voltage V0 thereof described above is controlled, and a gradient of the oxygen partial pressure in the measurement-object gas that is introduced into the second internal cavity 40 via the third diffusion control section 30 is consequently controlled so as to be always constant. In the case of a NOx sensor, the oxygen concentration in the second internal cavity 40 is held at a constant value of about 0.001 ppm by operation of the main pump cell 21 and the auxiliary pump cell 50.

The fourth diffusion control section 60 gives a predetermined diffusion resistance to the measurement-object gas the oxygen concentration (the oxygen partial pressure) of which has been controlled by operation of the auxiliary pump cell 50 in the second internal cavity 40 and guides the measurement-object gas toward the third internal cavity 61. The fourth diffusion control section 60 serves a function of limiting the amount of NOx that flows into the third internal cavity 61.

The third internal cavity 61 is formed as a space in which a process for measuring the concentration of a nitrogen oxide (NOx) in the measurement-object gas that is introduced via the fourth diffusion control section 60 is performed after the oxygen concentration (the oxygen partial pressure) is adjusted in the second internal cavity 40 in advance. The NOx concentration is mainly measured by operation of a measurement pump cell 41 in the third internal cavity 61.

The measurement pump cell 41 measures the NOx concentration in the measurement-object gas in the third internal cavity 61. The measurement pump cell 41 is an electrochemical pump cell that includes a measurement electrode 44 that is disposed on the upper surface of the first solid electrolyte layer 4 that faces the third internal cavity 61, the outer pump electrode 23, the second solid electrolyte layer 6, the spacer layer 5, and the first solid electrolyte layer 4.

The measurement electrode 44 is a porous cermet electrode that is composed of a material that has a higher level of ability to reduce the NOx components in the measurement-object gas than that of the inner pump electrode 22. The measurement electrode 44 also functions as a NOx reduction catalyst for reducing NOx contained in the atmosphere in the third internal cavity 61.

In the measurement pump cell 41, oxygen that is produced by decomposition of the nitrogen oxide in the atmosphere around the measurement electrode 44 is pumped out, and the amount thereof can be detected as a pump current Ip2.

In order to detect the oxygen partial pressure around the measurement electrode 44, an electrochemical sensor cell, that is, a measurement pump controlling oxygen partial pressure detection sensor cell 82 includes the first solid electrolyte layer 4, the third substrate layer 3, the measurement electrode 44, and the reference electrode 42. A variable power supply 46 is controlled based on an electromotive force (a voltage V2) that is detected by the measurement pump controlling oxygen partial pressure detection sensor cell 82.

The measurement-object gas that is guided into the second internal cavity 40 reaches the measurement electrode 44 in the third internal cavity 61 via the fourth diffusion control section 60 with the oxygen partial pressure controlled. The nitrogen oxide in the measurement-object gas around the measurement electrode 44 is reduced ($2NO \rightarrow N_2 + O_2$), and oxygen is produced. The produced oxygen is pumped by the measurement pump cell 41. At this time, a voltage Vp2 of the variable power supply 46 is controlled such that the voltage V2 that is detected by the measurement pump controlling oxygen partial pressure detection sensor cell 82 is constant (a target value). The amount of the oxygen that is produced around the measurement electrode 44 is proportional to the concentration of the nitrogen oxide in the measurement-object gas, and a nitrogen oxide concentration in the measurement-object gas is calculated by using the pump current Ip2 in the measurement pump cell 41.

An oxygen partial pressure detection device that includes a combination of the measurement electrode 44, the first solid electrolyte layer 4, the third substrate layer 3, and the reference electrode 42 and that serves as an electrochemical sensor cell can detect an electromotive force depending on a difference between the amount of oxygen that is produced by reducing the NOx components in the atmosphere around the measurement electrode 44 and the amount of oxygen that is contained in a reference atmosphere. This enables the concentration of the NOx components in the measurement-object gas to be obtained.

An electrochemical sensor cell 83 includes the second solid electrolyte layer 6, the spacer layer 5, the first solid electrolyte layer 4, the third substrate layer 3, the outer pump electrode 23, and the reference electrode 42. The oxygen partial pressure in the measurement-object gas outside the sensor can be detected by using an electromotive force (a voltage Vref) that is obtained by the sensor cell 83.

In the gas sensor 100 with this structure, the measurement-object gas the oxygen partial pressure of which is always held at a constant low value (a value that does not substantially affect the measurement of NOx) is provided to the measurement pump cell 41 by operation of the main pump cell 21 and the auxiliary pump cell 50. Accordingly, the NOx concentration in the measurement-object gas can be known based on the pump current Ip2 that flows with the result that oxygen that is produced by reducing NOx substantially in proportion to the NOx concentration in the measurement-object gas is pumped out by the measurement pump cell 41.

The sensor element 101 also includes a heater portion 70 that serves a temperature adjustment function of heating the sensor element 101 and maintaining temperature thereof in order to improve oxygen ion conductivity of the solid electrolyte. The heater portion 70 includes a heater connector electrode 71, a heater 72, a through-hole 73, a heater insulating layer 74, and a pressure diffusing hole 75. The heater portion 70 includes the first substrate layer 1, the second substrate layer 2, and the third substrate layer 3 that are composed of ceramics. The heater portion 70 is a ceramic heater that includes the heater 72 and the third substrate layer 3 and the second substrate layer 2 surrounding the heater 72. As illustrated in FIG. 2, the heater 72 includes a heat generation portion 76 and a lead portion 85.

The heater connector electrode 71 is formed so as to be in contact with the lower surface of the first substrate layer 1. Connecting the heater connector electrode 71 to an external power supply enables electricity to be supplied from the outside to the heater portion 70.

The heat generation portion 76 of the heater 72 is an electric resistor that is formed such that the electric resistor is interposed between the second substrate layer 2 and the third substrate layer 3 in the vertical direction. The lead portion 85 of the heater 72 is connected to the heater connector electrode 71 with the through-hole 73 interposed therebetween, and the heat generation portion 76 generates heat with the result that electricity is supplied from the outside via the heater connector electrode 71 to heat the solid electrolyte of which the sensor element 101 is composed and to maintain the temperature thereof.

The heat generation portion 76 of the heater 72 is embedded across a region from the first internal cavity 20 to the third internal cavity 61 and can adjust the temperature of the entire sensor element 101 to a temperature at which the solid electrolyte described above is activated.

The heater insulating layer 74 is composed of an insulator such as alumina on the upper and lower surfaces of the heater 72. The heater insulating layer 74 is formed to provide electrical insulation between the second substrate layer 2 and the heater 72 and electrical insulation between the third substrate layer 3 and the heater 72.

The pressure diffusing hole 75 is formed so as to extend through the third substrate layer 3 and the air introduction layer 48 and so as to communicate with the reference gas introduction space 43 and is formed to relieve an increase in inner pressure due to an increase in temperature in the heater insulating layer 74.

The heat generation portion 76 and the lead portion 85 of the heater 72 will be described in detail. The heat generation portion 76 is a resistive heating element and has a belt-like shape in a one-stroke pattern such that both ends are connected to the lead portion 85 as illustrated in FIG. 2. The heat generation portion 76 includes bend portions 77 and linear portions 78. The bend portions 77 include a first bend portion 77a, a second bend portion 77b, and a third bend portion 77c. The linear portions 78 include a first outer linear portion 78a, a second outer linear portion 78b, a first inner linear portion 79a, and a second inner linear portion 79b. The multiple bend portions 77 and the multiple linear portions 78 are electrically connect in series. Specifically, the first outer linear portion 78a, the first bend portion 77a, the first inner linear portion 79a, the second bend portion 77b, the second inner linear portion 79b, the third bend portion 77c, and the second outer linear portion 78b are connected in series in this order from a first lead 85a, and the second outer linear portion 78b is connected to a second lead 85b. The heat generation portion 76 is bilaterally symmetric.

The multiple linear portions 78 are arranged in the transverse direction (the left-right direction) of the sensor element 101. Specifically, the first outer linear portion 78a, the first inner linear portion 79a, the second inner linear portion 79b, and the second outer linear portion 78b are arranged in this order from the left to the right of the sensor element 101. For this reason, the first inner linear portion 79a and the second inner linear portion 79b are located between the first outer linear portion 78a and the second outer linear portion 78b in the left-right direction. The first outer linear portion 78a, the second outer linear portion 78b, the first inner linear portion 79a, and the second inner linear portion 79b are arranged so as to have a length direction parallel with the longitudinal direction. A rear end of the first outer linear portion 78a is connected to the first lead 85a. A rear end of the second outer linear portion 78b is connected to the second lead 85b. The first inner linear portion 79a includes a front side part 79a1, a rear side part 79a3 that is located at the rear of the front side part 79a1, and a connection part 79a2 that connects the front side part 79a1 and the rear side part 79a3 to each other. The second inner linear portion 79b includes a front side part 79b1, a rear side part 79b3 that is located at the rear of the front side part 79b1, and a connect part 79b2 that connects the front side part 79b1 and the rear side part 79b3 to each other.

Regarding the linear portions 78, the case of "to be arranged so as to have a length direction parallel with the longitudinal direction" includes the case where the length direction is parallel with the longitudinal direction (the front-rear direction) of the sensor element 101 and the case where the length direction inclines with respect to the longitudinal direction (the front-rear direction) of the sensor element 101. According to the present embodiment, for example, the first outer linear portion 78a, the second outer linear portion 78b, the front side part 79a1, the rear side part 79a3, the front side part 79b1, and the rear side part 79b3 have a length direction parallel with the longitudinal direction of the sensor element 101. The connection part 79a2 and the connect part 79b2 have a length direction inclining with respect to the longitudinal direction of the sensor element 101.

The multiple bend portions 77 connect the respective linear portions 78 adjacent to each other in the left-right direction. Specifically, the first bend portion 77a connects the first outer linear portion 78a and the first inner linear portion 79a to each other at a first end (a front here) in the longitudinal direction. The second bend portion 77b connects the first inner linear portion 79a and the second inner linear portion 79b to each other at a second end (a rear here) in the longitudinal direction. The third bend portion 77c connects the second inner linear portion 79b and the second outer linear portion 78b to each other at the first end (the front here) in the longitudinal direction. The first to third bend portions 77a to 77c bend so as to be curved and have an arc shape of a semicircle. The first to third bend portions 77a to 77c may bend so as to be folded.

Positional relationships between the heat generation portion 76 and the internal cavities (the first internal cavity 20, the second internal cavity 40, and the third internal cavity 61 here) of the measurement-object gas flow section are adjusted. This will be described. The first internal cavity 20 is an example of a main pump chamber, the second internal cavity 40 is an example of an auxiliary pump chamber, and the third internal cavity 61 is an example of a measurement chamber. FIG. 2 illustrates a main pump chamber projection region Ap on which the first internal cavity 20 is projected toward the heat generation portion 76 in the thickness direction (a downward direction here) by using a frame of a one-dot chain line. Similarly, FIG. 2 also illustrates an auxiliary pump chamber projection region Aq and a measurement chamber projection region Am on which the second internal cavity 40 and the third internal cavity 61 are projected toward the heat generation portion 76 by using frames of one-dot chain lines. According to the present embodiment, as illustrated in FIG. 2, the main pump chamber projection region Ap, the auxiliary pump chamber projection region Aq, and the measurement chamber projection region Am are rectangular regions. That is, according to the present embodiment, the shapes of the first internal cavity 20, the second internal cavity 40, and the third internal cavity 61 are rectangular shapes in a top view.

At least a part of the first inner linear portion 79a and a part of the second inner linear portion 79b of the heat generation portion 76 overlap the main pump chamber projection region Ap. Specifically, the front side part 79a1 of the first inner linear portion 79a and the front side part 79b1 of the second inner linear portion 79b at least partly overlap the main pump chamber projection region Ap. In other words, the first inner linear portion 79a and the second inner linear portion 79b (in particular, the front side part 79a1 and the front side part 79b1) are located right below the first internal cavity 20. At least a part of the first inner linear portion 79a and a part of the second inner linear portion 79b of the heat generation portion 76 overlap the auxiliary pump chamber projection region Aq. Specifically, the rear side part 79a3 of the first inner linear portion 79a and the rear side part 79b3 of the second inner linear portion 79b at least partly overlap the auxiliary pump chamber projection region Aq. In other words, the first inner linear portion 79a and the second inner linear portion 79b (in particular, the rear side part 79a3 and the rear side part 79b3) are located right below the second internal cavity 40. According to the present embodiment, parts of the second bend portion 77b, specifically, parts of the second bend portion 77b that are connected to the rear side part 79a3 and the rear side part 79b3 overlap the auxiliary pump chamber projection region Aq. At least a part of the heat generation portion 76 overlaps the measurement chamber projection region Am. Specifically, at least a part of the second bend portion 77b of the heat generation portion 76 overlaps the measurement chamber projection region Am. According to the present embodiment, the connection part 79a2 and the connect part 79b2 are located between the main pump chamber projection region Ap and the auxiliary pump chamber projection region Aq in the front-rear direction but overlap neither the main pump chamber projection region Ap nor the auxiliary pump chamber projection region Aq. The first bend portion 77a, the third bend portion 77c, the first outer linear portion 78a, and the second outer linear portion 78b overlap none of the main pump chamber projection region Ap, the auxiliary pump chamber projection region Aq, and the measurement chamber projection region Am. According to the present embodiment, the heat generation portion 76 is bilaterally symmetric, and the central axis of the heat generation portion 76 in the left-right direction, the central axis of the main pump chamber projection region Ap in the left-right direction, the central axis of the auxiliary pump chamber projection region Aq in the left-right direction, and the central axis of the measurement chamber projection region Am in the left-right direction match each other.

A distance X1 in the transverse direction (the left-right direction) between the first inner linear portion 79a and the second inner linear portion 79b of the heat generation portion 76 at a portion that overlaps the main pump chamber projection region Ap is equal to or more than ⅓ of the width Wp of the main pump chamber projection region Ap in the transverse direction. That is, $X1 \geq \frac{1}{3} \times Wp$ is satisfied. According to the present embodiment, the front side part 79a1 and the front side part 79b1 of the heat generation portion 76 overlap the main pump chamber projection region Ap, and consequently, the distance X1 is a distance in the left-right direction between the front side part 79a1 and the front side part 79b1. According to the present embodiment, the front side part 79a1 and the front side part 79b1 are parallel with each other in the length direction, and consequently, the distance in the left-right direction between the front side part 79a1 and the front side part 79b1 is constant (equal to the distance X1). In the case where the distance therebetween in the left-right direction is not constant, for example, in the case where the front side part 79a1 and the front side part 79b1 are not parallel with each other, the distance X1 is the average value of a distance in the transverse direction (the left-right direction) between the part of the first inner linear portion 79a and the part of the second inner linear portion 79b that overlap the main pump chamber projection region Ap.

A distance X2 in the transverse direction (the left-right direction) between the first inner linear portion 79a and the second inner linear portion 79b of the heat generation portion 76 at a portion that overlaps the auxiliary pump chamber projection region Aq is equal to or more than 0.4 times the width Wp of the main pump chamber projection region Ap in the transverse direction. That is, $X2 \geq 0.4 Wp$ is satisfied. According to the present embodiment, the rear side part 79a3 and the rear side part 79b3 of the heat generation portion 76 overlap the auxiliary pump chamber projection region Aq, and consequently, the distance X2 is a distance in the left-right direction between the rear side part 79a3 and the rear side part 79b3. According to the present embodiment, the rear side part 79a3 and the rear side part 79b3 are parallel with each other in the length direction, and consequently, the distance in the left-right direction between the rear side part 79*a*3 and the rear side part 79*b*3 is constant (equal to the distance X2). In the case where the distance therebetween in the left-right direction is not constant, for example, in the case where the rear side part 79*a*3 and the rear side part 79*b*3 are not parallel with each other, the distance X2 is the average value of a distance in the transverse direction (the left-right direction) between the part of the first inner linear portion 79*a* and the part of the second inner linear portion 79*b* that overlap the auxiliary pump chamber projection region Aq.

When the conditions described above, that is, "X1≥⅓× Wp" and "X2≥0.4Wp" are satisfied, a stress that is applied to the vicinity of the internal cavities (the first internal cavity 20, the second internal cavity 40, and the third internal cavity 61) of the sensor element 101 can be reduced when the heat generation portion 76 generates heat. The distance X1 is preferably equal to or more than 0.4 times the width Wp and is more preferably more than 0.4 times the width Wp. The distance X1 may be equal to or more than ⅔ times the width Wp. The distance X1 is preferably equal to or less than the width Wp and may be less than the width Wp. The distance X2 may be equal to or more than ⅔ times the width Wp. The distance X2 is preferably equal to or less than a width Wq and may be less than the width Wq, where the width Wq is the width of the auxiliary pump chamber projection region Aq in the left-right direction. According to the present embodiment, as illustrated in FIG. 2, the distance X2 is longer than the distance X1.

According to the present embodiment, the heat generation portion 76 is bilaterally symmetric, and the central axis of the heat generation portion 76 in the left-right direction and the central axis of the main pump chamber projection region Ap in the left-right direction match each other. For this reason, the heat generation portion 76 is not located in a region that is located at the center in the left-right direction in the main pump chamber projection region Ap and that has a width equal to the distance X1. For example, when X1>⅓×Wp described above is satisfied, the heat generation portion 76 is not located in a region (that is, a central region among three regions obtained by equally dividing the main pump chamber projection region Ap in the left-right direction) that is located at the center in the left-right direction in the main pump chamber projection region Ap and that has a width of ⅓×Wp. In other words, the heat generation portion 76 is not located right below a region of the main pump chamber (the first internal cavity 20) that is located at the center in the left-right direction and that has a width of ⅓×Wp. Similarly, when X1>0.4Wp is satisfied, the heat generation portion 76 is not located in a region that is located at the center in the left-right direction in the main pump chamber projection region Ap and that has a width of 0.4Wp.

The heat generation portion 76 is bilaterally symmetric, and the central axis of the heat generation portion 76 in the left-right direction and the central axis of the main pump chamber projection region Ap in the left-right direction match each other. For this reason, when the distance X1 is equal to or less than the width Wp, at least the part of the first inner linear portion 79*a* and the part of the second inner linear portion 79*b* (in particular, the front side part 79*a*1 and the front side part 79*b*1 here) overlap the main pump chamber projection region Ap.

According to the present embodiment, the heat generation portion 76 is bilaterally symmetric, and the central axis of the heat generation portion 76 in the left-right direction and the central axis of the auxiliary pump chamber projection region Aq in the left-right direction match each other. For this reason, the heat generation portion 76 is not located in a region that is located at the center in the left-right direction in the auxiliary pump chamber projection region Aq and that has a width equal to the distance X2. In other words, the heat generation portion 76 is not located right below a region of the auxiliary pump chamber (the second internal cavity 40) that is located at the center in the left-right direction and that has a width equal to X2.

The heat generation portion 76 is bilaterally symmetric, and the central axis of the heat generation portion 76 in the left-right direction and the central axis of the auxiliary pump chamber projection region Aq in the left-right direction match each other. For this reason, when the distance X2 is equal to or less than the width Wq, at least the part of the first inner linear portion 79*a* and the part of the second inner linear portion 79*b* (in particular, the rear side part 79*a*3 and the rear side part 79*b*3 here) overlap the auxiliary pump chamber projection region Aq.

According to the present embodiment, the heat generation portion 76 is composed of cermet (such as cermet of platinum (Pt) and alumina ($Al_2O_3$)) that contains precious metal and ceramics. The heat generation portion 76 is not limited to cermet, provided that the heat generation portion 76 contains a conductive material such as precious metal. Examples of precious metal that is used for the heat generation portion 76 include metal of at least one of platinum, rhodium (Rh), gold (Au), and palladium (Pd) or an alloy thereof.

The resistance value per unit length of a pump chamber overlapping portion that overlaps the main pump chamber projection region Ap and the auxiliary pump chamber projection region Aq in the heat generation portion 76 is referred to as a unit resistance value R1 [μΩ/mm]. The resistance value per unit length of a measurement chamber overlapping portion that overlaps the measurement chamber projection region Am in the heat generation portion 76 is referred to as a unit resistance value R3 [μΩ/mm]. In this case, as for the heat generation portion 76, a unit resistance value ratio R3/R1 is less than 1 at least at a temperature in a temperature range of no less than 700° C. and no more than 900° C. at which there is a possibility that the heat generation portion 76 in use is heated. In other words, the unit resistance value R3 is smaller than the unit resistance value R1 at least at a temperature in a temperature range of no less than 700° C. and no more than 900° C. According to the present embodiment, the pump chamber overlapping portion includes parts that overlap the main pump chamber projection region Ap in the front side part 79*a*1 and the front side part 79*b*1, parts that overlap the auxiliary pump chamber projection region Aq in the rear side part 79*a*3 and the rear side part 79*b*3, and parts that overlap the auxiliary pump chamber projection region Aq in the second bend portion 77*b*. According to the present embodiment, the measurement chamber overlapping portion is a part of the second bend portion 77*b* that overlaps the measurement chamber projection region Am. The length direction of the heat generation portion 76 is the axial direction of the heat generation portion 76, in other words, a direction in which an electric current flows. The unit resistance value R1 is the average resistance value per unit length of the pump chamber overlapping portion. Similarly, the unit resistance value R3 is the average resistance value per unit length of the measurement chamber overlapping portion. For this reason, a part of the measurement chamber overlapping portion may have a resistance value per unit length larger than that of the pump chamber overlapping portion, provided that the resistance value per unit length is smaller than that of the measurement chamber overlapping portion as a whole.

However, the resistance value per unit length is preferably smaller than the unit resistance value R1 at any position on the measurement chamber overlapping portion.

When the unit resistance value R3 is too large, a difference between temperature in the vicinity of the first internal cavity 20 and the second internal cavity 40 and temperature in the vicinity of the third internal cavity 61 is too small, and the precision of detection of the NOx concentration decreases in some cases. When the unit resistance value ratio R3/R1 is less than 1, the precision of detection can be inhibited from decreasing. The unit resistance value ratio R3/R1 at least at a temperature in the temperature range described above is preferably 0.8 or less, more preferably 0.7 or less, further preferably 0.65 or less. The unit resistance value ratio R3/R1 at least at a temperature in the temperature range described above may be 0.5 or more.

According to the present embodiment, the materials of the first inner linear portion 79a, the second inner linear portion 79b, and the second bend portion 77b are the same (the cermet that contains platinum described above), and a sectional area S1 [mm$^2$] of the heat generation portion 76 perpendicular to the length direction of the pump chamber overlapping portion is smaller than a sectional area S3 [mm$^2$] perpendicular to the length direction of the measurement chamber overlapping portion. That is, as for the heat generation portion 76, the sectional area ratio S1/S3 is less than 1. In this way, the unit resistance value ratio R3/R1 is less than 1 at any temperature in a temperature range of no less than 700° C. and no more than 900° C. The sectional area ratio S1/S3 is preferably 0.8 or less, more preferably 0.7 or less, further preferably 0.65 or less. The sectional area ratio S1/S3 may be 0.5 or more. For example, the sectional area ratio S1/S3 is adjusted at least by decreasing the width W1 of the pump chamber overlapping portion to a width less than the width W3 of the measurement chamber overlapping portion or decreasing the thickness D1 of the pump chamber overlapping portion to a thickness less than the thickness D3 of the measurement chamber overlapping portion. The values of the sectional areas S1 and S3, the widths W1 and W3, and the thicknesses D1 and D3 are average values of those of the pump chamber overlapping portion and the measurement chamber overlapping portion as in the unit resistance values R1 and R3.

According to the present embodiment, the first inner linear portion 79a, the second inner linear portion 79b, and the second bend portion 77b have the same thickness at any position. The first inner linear portion 79a and the second inner linear portion 79b have the same width at any position. The widths of the parts of the second bend portion 77b that are connected to the first inner linear portion 79a and the second inner linear portion 79b increase as the positions from the first inner linear portion 79a and the second inner linear portion 79b increase, and the other part other than the connected parts (including the part that overlaps the measurement chamber projection region Am) has a constant width. For this reason, the width W1 according to the present embodiment is slightly more than the widths of the first inner linear portion 79a and the second inner linear portion 79b because the parts of the second bend portion 77b are included in the pump chamber overlapping portion. The width W3 is the same as the width of the other part of the second bend portion 77b other than the parts that are connected to the first inner linear portion 79a and the second inner linear portion 79b. When the width W1 is less than the width W3, the sectional area ratio S1/S3 is less than 1. A ratio W1/W3 between the width W1 and the width W3 is preferably 0.8 or less, more preferably 0.7 or less, and further preferably 0.65 or less. The ratio W1/W3 may be 0.5 or more. The widths W1 and W3 may be no less than 0.05 mm and no more than 1.5 mm. The thicknesses D1 and D3 may be no less than 0.003 mm and no more than 0.1 mm. The width W1 may be no less than 0.3 mm and no more than 0.4 mm. The width W3 may be no less than 0.5 mm and no more than 0.6 mm.

The distance X1 may be 0.67 mm or more, may be 0.8 mm or more, or may be 0.86 mm or more. The distance X1 may be 2 mm or less, may be less than 2 mm, may be 1.67 mm or less, or may be 1.34 mm or less. The distance X2 may be 0.8 mm or more or may be 0.86 mm or more. The distance X2 may be 2 mm or less, may be less than 2 mm, or may be 1.34 mm or less. The width Wp (equal to the width of the first internal cavity 20) of the main pump chamber projection region Ap is, for example, no less than 1.5 mm and no more than 3 mm. The width Wq (equal to the width of the second internal cavity 40) of the auxiliary pump chamber projection region Aq is, for example, no less than 1.2 mm and no more than 2.4 mm. The width Wm (equal to the width of the third internal cavity 61) of the measurement chamber projection region Am is, for example, no less than 0.9 mm and no more than 1.8 mm. A length from the front end of the sensor element 101 to the rear end of the third internal cavity 61, that is, the length of the measurement-object gas flow section is, for example, no less than 7.5 mm and no more than 9 mm. According to the present embodiment, Wp>Wq>Wm is satisfied.

The lead portion 85 includes the first lead 85a that is disposed on the left behind the heat generation portion 76 and the second lead 85b that is disposed on the right behind the heat generation portion 76. The first and second leads 85a and 85b are leads for energizing the heat generation portion 76 and are connected to the heater connector electrode 71. The first lead 85a is a positive electrode lead. The second lead 85b is a negative electrode lead. When a voltage is applied between the first and second leads 85a and 85b, an electric current flows through the heat generation portion 76, and the heat generation portion 76 generates heat. The lead portion 85 is a conductor and has a resistance value per unit length smaller than that of the heat generation portion 76. For this reason, the lead portion 85 scarcely generates heat during energizing unlike the heat generation portion 76. For example, the lead portion 85 is composed of a material that has volume resistivity lower than that of the heat generation portion 76, has a sectional area larger than that of the heat generation portion 76, and consequently has a resistance value per unit length smaller than that of the heat generation portion 76. According to the present embodiment, the lead portion 85 has a proportion of precious metal higher than that of the heat generation portion 76 and consequently has volume resistivity lower than that of the heat generation portion 76, and the lead portion 85 has a width more than that of the heat generation portion 76 and consequently has a sectional area wider than that of the heat generation portion 76.

A method of manufacturing the gas sensor 100 thus configured will now be described. Six ceramic green sheets that are not fired and that contain an oxygen-ion-conductive solid electrolyte such as zirconia as a ceramic component are first prepared. Sheet holes used for positioning during printing or stacking and required through-holes, for example, are formed in the green sheets in advance. A space to be the measurement-object gas flow section is formed in the green sheet to be the spacer layer 5 by, for example, a punching process. Pattern printing processes in which various patterns are formed on the ceramic green sheets so as to correspond to the first substrate layer 1, the second substrate layer 2, the third substrate layer 3, the first solid electrolyte layer 4, the spacer layer 5, and the second solid electrolyte layer 6 and drying processes are performed. Specific patterns to be formed are patterns such as the electrodes described above, lead wires that are connected to the electrodes, the air introduction layer 48, and the heater 72. The pattern printing is performed by applying pattern forming paste that is prepared depending on characteristics required for subjects to be formed to the green sheets by using a known screen printing technique. A mixture of, for example, the material (such as precious metal and ceramic particles) of the heater 72 described above, an organic binder, and an organic solvent is used for the pattern forming paste to be the heater 72.

At this time, the pattern to be the heater 72 is formed such that the unit resistance value ratio R3/R1 is less than 1, for example, such that the sectional area ratio S1/S3 is less than 1. To satisfy width W1<width W3, for example, a mask having a shape that enables such a pattern to be formed is used. To satisfy thickness D1<thickness D3, for example, the viscosity of the paste for forming the pattern of a portion (such as the second bend portion 77b) to be the measurement chamber overlapping portion is increased to viscosity higher than that of the pattern of a portion (such as the first inner linear portion 79a and the second inner linear portion 79b) to be the pump chamber overlapping portion, or the number of times printing is performed when the pattern of the portion to be the measurement chamber overlapping portion is formed is increased.

After the various patterns are thus formed, the green sheets are dried. The drying process is performed by using a known drying device. After the pattern printing and drying are finished, adhesive paste for stacking and sticking the green sheets corresponding to the layers to each other is printed and dried. The green sheets on which the adhesive paste has been formed are stacked in a predetermined order while the positions thereof are set by using the sheet holes, and a pressure bonding process is performed in a manner in which the green sheets are bonded by pressure bonding under predetermined temperature and pressure conditions and are formed into a layered body. The layered body thus obtained includes multiple sensor elements 101. The layered body is cut in the size of each sensor element 101. A piece of the cut layered body is fired at a predetermined firing temperature, and the sensor element 101 is obtained thereto.

The sensor element 101 is obtained in the above manner, and the gas sensor 100 is obtained in a manner in which a sensor assembly into which the sensor element 101 is incorporated is manufactured, and a protective cover, for example, is attached.

As for the gas sensor 100 thus configured, the heater 72 is connected to a power supply (for example, an alternator of an automobile) during use with the heater connector electrode 71 interposed therebetween, and a direct voltage (for example, 12 to 14 V) is applied between the first lead 85a and the second lead 85b. An electric current flows through the heat generation portion 76 by applying the voltage, and the heat generation portion 76 generates heat. Consequently, the temperature of the entire sensor element 101 is adjusted to a temperature (for example, 700° C. to 900° C.) at which the solid electrolyte (the layers 1 to 6) is activated. In this state, the measurement-object gas is introduced from the gas inlet 10 to the measurement-object gas flow section, and consequently, the measurement-object gas passes through the first diffusion control section 11, the buffer space 12, and the second diffusion control section 13 and reaches the first internal cavity 20. Subsequently, the oxygen concentration of the measurement-object gas is adjusted in the first internal cavity 20 and the second internal cavity 40 by using the main pump cell 21 and the auxiliary pump cell 50, and the measurement-object gas after adjustment reaches the third internal cavity 61. The NOx concentration in the measurement-object gas is detected based on the pump current Ip2 when the measurement pump cell 41 pumps out oxygen in the third internal cavity 61.

At this time, the temperature of the heat generation portion 76 is high, and a stress is applied to the vicinity of the internal cavities (the first internal cavity 20, the second internal cavity 40, and the third internal cavity 61) of the sensor element 101 in some cases. This is presumably caused by a difference in temperature between a location below the internal cavities and a location above the internal cavities in the sensor element 101. As for the sensor element 101 according to the present embodiment, however, "X1≥⅓×Wp" and "X2≥0.4Wp" described above are satisfied, and consequently, a stress that is applied to the vicinity of the internal cavities of the sensor element 101 can be reduced when the heat generation portion 76 generates heat. This is presumably because satisfying the conditions described above for the distances X1 and X2 enables the vicinity of a central portion in the left-right direction below the internal cavities to be inhibited from being overheated and enables a difference in temperature between the location below the internal cavities and the location above the internal cavities to be decreased. When the distance X1 is more than 0.4 times the width Wp, the effect of reducing the stress described above is enhanced.

When "X1≥⅓×Wp" and "X2≥0.4Wp" are satisfied, a stress that is applied to an outer circumferential portion (in particular, a lower surface that is an outer circumferential surface of the sensor element 101 near the heater 72) of the sensor element 101 can also be reduced. This is presumably because satisfying the conditions described above for the distances X1 and X2 enables the vicinity of a central portion of the lower surface of the sensor element 101 in the left-right direction to be inhibited from being overheated and enables a difference in temperature between the central portion of the lower surface in the left-right direction and the other portion to be decreased.

According to the present embodiment, the distance X1 is equal to or less than the width Wp, and at least the part of the first inner linear portion 79a and the part of the second inner linear portion 79b (in particular, the front side part 79a1 and the front side part 79b1 here) overlap the main pump chamber projection region Ap. For this reason, the solid electrolyte in the vicinity of the main pump chamber (the first internal cavity 20 here) can be sufficiently heated by the heat generation portion 76, and the main pump cell 21 can sufficiently function. Similarly, the distance X2 is equal to or less than the width Wq, and at least the part of the first inner linear portion 79a and the part of the second inner linear portion 79b (in particular, the rear side part 79a3 and the rear side part 79b3 here) overlap the auxiliary pump chamber projection region Aq. For this reason, the solid electrolyte in the vicinity of the auxiliary pump chamber (the second internal cavity 40 here) can be sufficiently heated by the heat generation portion 76, and the auxiliary pump cell 50 can sufficiently function. In the case where the main pump cell 21 and the auxiliary pump cell 50 insufficiently function, the oxygen concentration in the measurement-object gas is not sufficiently adjusted, and the precision of detection of the NOx concentration decreases in some cases. According to the present embodiment, however, the distance X1 is equal to or less than the width Wp, the distance X2 is equal to or less than the width Wq, and consequently, the precision of detection of the NOx concentration can be inhibited from decreasing.

According to the present embodiment, at least the part of the heat generation portion 76 (the second bend portion 77b here) overlaps the measurement chamber projection region Am. For this reason, the solid electrolyte in the vicinity of the measurement chamber (the third internal cavity 61 here) can be sufficiently heated, and the measurement pump cell 41 can sufficiently function. Also, in this way, the precision of detection of the NOx concentration can be inhibited from decreasing.

When the unit resistance value ratio R3/R1 is less than 1 at least at a temperature in a temperature range of no less than 700° C. and no more than 900° C., the precision of detection of the NOx concentration can be inhibited from decreasing. This will be described in detail. When the heat generation portion 76 generates heat, (temperature Tp and temperature Tq)>temperature Tm is preferably satisfied, and temperature Tp>temperature Tq>temperature Tm is more preferably satisfied, where the temperatures Tp, Tq, and Tm [° C.] are respective temperatures in the vicinity of the first internal cavity 20, the second internal cavity 40, and the third internal cavity 61. The reason is as follows. The vicinity of the inner pump electrode 22, that is, the first internal cavity 20 has an oxygen concentration higher than that of the vicinity of the measurement electrode 44 because the measurement-object gas before the oxygen concentration is adjusted by the main pump cell 21 flows into from the gas inlet 10. The vicinity of the auxiliary pump electrode 51, that is, the second internal cavity 40 has an oxygen concentration higher than that of the vicinity of the measurement electrode 44 because the measurement-object gas before the oxygen concentration is adjusted by the auxiliary pump cell 50 flows into from the first internal cavity 20. For this reason, the temperature Tp in the vicinity of the first internal cavity 20 and the temperature Tq in the vicinity of the second internal cavity 40 are preferably higher than the temperature Tm, and the inner pump electrode 22, the auxiliary pump electrode 51, and the solid electrolyte layers in the vicinity thereof are preferably further activated to make it possible to pump out a large amount of oxygen by the main pump cell 21 and the auxiliary pump cell 50. The vicinity of the measurement electrode 44, that is, the third internal cavity 61 has an oxygen concentration lower than those of the first internal cavity 20 and the second internal cavity 40. For this reason, in some cases, hydrogen and carbon monoxide are generated, for example, due to the reduction of carbon dioxide and water in the measurement-object gas, and these chemically react with oxygen in NOx, which causes the precision of measurement to decrease. Components other than the specific gas (NOx) are more likely to be reduced as temperature increases. For this reason, the temperature Tm is preferably not too high. For the reasons described above, (temperature Tp and temperature Tq)>temperature Tm is preferably satisfied. The first internal cavity 20 is located upstream of the second internal cavity 40 in the measurement-object gas flow section, and the oxygen concentration of the first internal cavity 20 is higher than that of the second internal cavity 40. Accordingly, the temperature Tp in the vicinity of the first internal cavity 20 is preferably higher than the temperature Tq in the vicinity of the second internal cavity 40, and the inner pump electrode 22 and the solid electrolyte layers in the vicinity thereof are preferably further activated. For this reason, temperature Tp>temperature Tq>temperature Tm is preferably satisfied. When the unit resistance value R3 is too large, the temperature Tm is too high, the relationship of (temperature Tp and temperature Tq)>temperature Tm is not satisfied, and the precision of measurement of the NOx concentration decreases in some cases. When the unit resistance value ratio R3/R1 is less than 1, the unit resistance value R3 is not too large, and the precision of detection can be inhibited from decreasing. When the temperature Tm is high, the temperature Tq in the vicinity of the second internal cavity 40 near the third internal cavity 61 is likely to increase. Consequently, temperature Tp<temperature Tq>temperature Tm is satisfied, the relationship of temperature Tp>temperature Tq>temperature Tm is not satisfied, and the pumping ability of the main pump cell 21 lacks in some cases. When the unit resistance value ratio R3/R1 is less than 1, however, the pumping ability of the main pump cell 21 is likely to sufficiently increase.

The correspondence relationships between components according to the present embodiment and components according to the present invention will now be clarified. The layers 1 to 6 according to the present embodiment correspond to an element body according to the present invention, the first internal cavity 20 corresponds to a main pump chamber, the main pump cell 21 corresponds to a main pump cell, the second internal cavity 40 corresponds to an auxiliary pump chamber, the auxiliary pump cell 50 corresponds to an auxiliary pump cell, the third internal cavity 61 corresponds to a measurement chamber, the measurement pump cell 41 corresponds to a measurement pump cell, the heat generation portion 76 corresponds to a heating element, the first outer linear portion 78a corresponds to a first outer linear portion, the second outer linear portion 78b corresponds to a second outer linear portion, the first inner linear portion 79a corresponds to a first inner linear portion, the second inner linear portion 79b corresponds to a second inner linear portion, the first to third bend portions 77a to 77c correspond to first to third bend portions, the main pump chamber projection region Ap corresponds to a main pump chamber projection region, and the auxiliary pump chamber projection region Aq corresponds to an auxiliary pump chamber projection region.

As for the gas sensor 100 according to the present embodiment described in detail above, the distance X1 is equal to or more than ⅓ of the width Wp, the distance X2 is equal to or more than 0.4 times the width Wp, and consequently, a stress that is applied to the vicinity of the internal cavities (the main pump chamber, the auxiliary pump chamber, and the measurement chamber) can be reduced when the heating element generates heat. When the distance X1 is more than 0.4 times the width Wp, the effect of reducing the stress described above is enhanced. When the unit resistance value ratio R3/R1 is less than 1 at least at a temperature in a temperature range of no less than 700° C. and no more than 900° C., the precision of detection of the NOx concentration can be inhibited from decreasing.

It goes without saying that the present invention is not limited to the embodiment described above and can be carried out in various aspects within the technical scope of the present invention.

Figure 3:
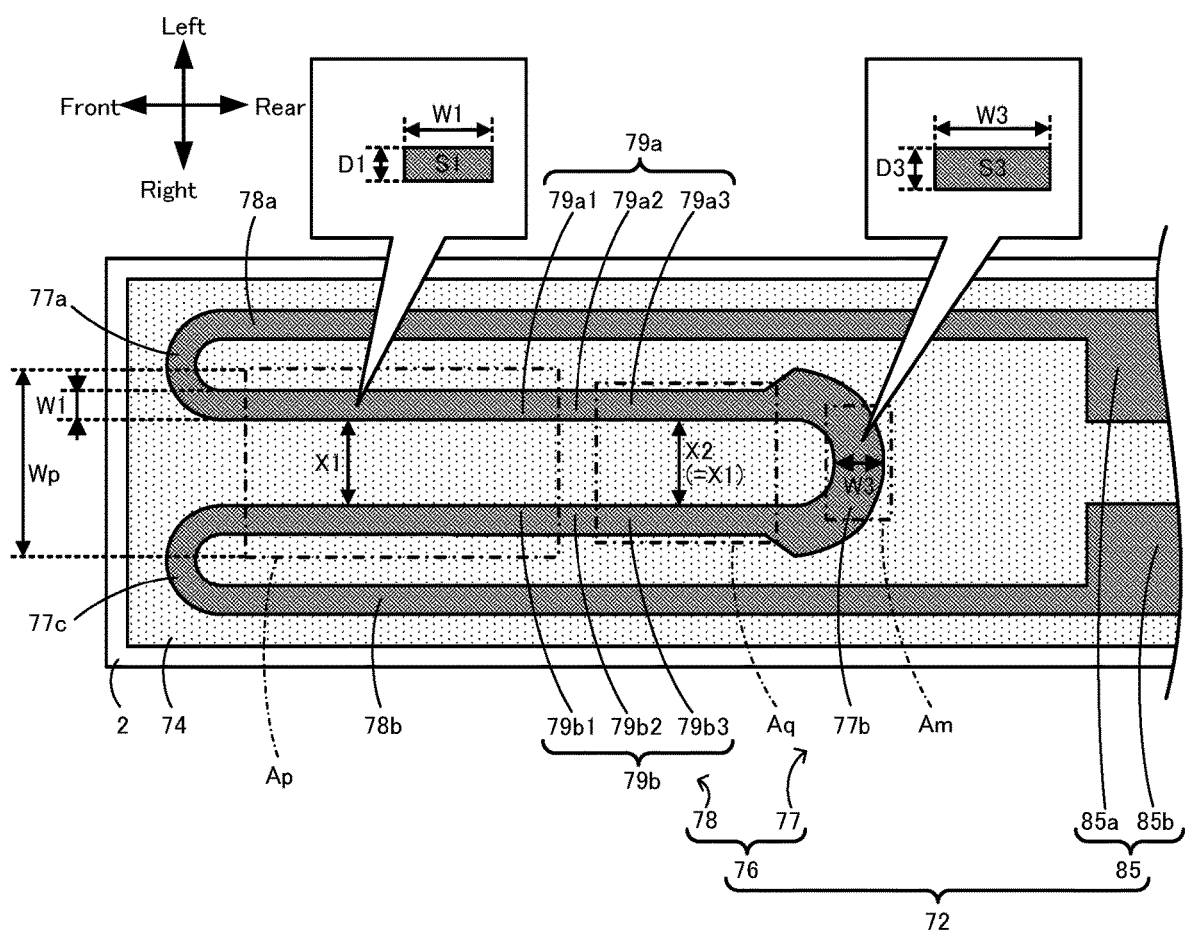
FIG. 3 illustrates a heater 72 according to a modification.

For example, according to the embodiment described above, the distance X2 is longer than the distance X1, but this is not a limitation. For example, as illustrated in FIG. 3, the distance X1 may be equal to the distance X2. Also, in this case, when "X1≥⅓×Wp" and "X2≥0.4Wp" are satisfied, a stress that is applied to the vicinity of the internal cavities of the sensor element 101 can be reduced when the heat generation portion 76 generates heat. In the case of FIG. 3, X1=X2 is satisfied, and consequently, "X1≥0.4Wp" is satisfied. In an example in FIG. 3, the front side part 79a1, the connection part 79a2, and the rear side part 79a3 of the first inner linear portion 79a are linearly extend, and consequently, the shapes of the front side part 79a1, the connection part 79a2, and the rear side part 79a3 cannot be distinguished from each other. The same is true for the front side part 79b1, the connect part 79b2, and the rear side part 79b3 of the second inner linear portion 79b.

Figure 4:
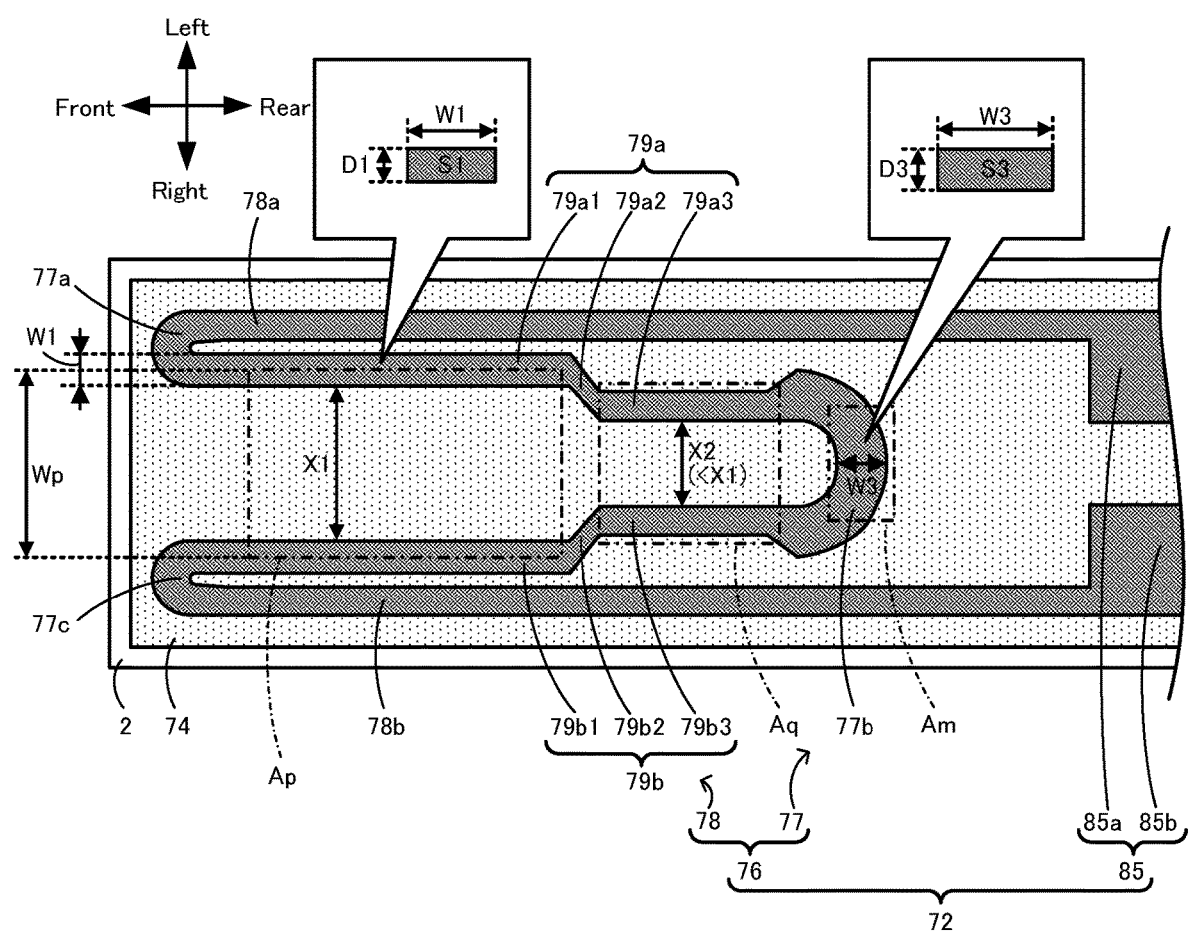
FIG. 4 illustrates the heater 72 according to a modification.

Alternatively, as illustrated in FIG. 4, the distance X1 may be longer than the distance X2. Also, in this case, when "X1≥⅓×Wp" and "X2≥0.4Wp" are satisfied, a stress that is applied to the vicinity of the internal cavities of the sensor element 101 can be reduced when the heat generation portion 76 generates heat. In the case of FIG. 4, X1>X2 is satisfied, and consequently, "X1>0.4Wp" is satisfied.

According to the embodiment described above, the sectional area ratio S1/S3 is less than 1, and consequently, the unit resistance value ratio R3/R1 is less than 1, but this is not a limitation. For example, a volume resistivity ratio $\rho 3/\rho 1$ that is a ratio between the volume resistivity $\rho 1$ [$\mu \Omega \cdot cm$] of the pump chamber overlapping portion and the volume resistivity $\rho 3$ [$\mu \Omega \cdot cm$] of the measurement chamber overlapping portion may be less than 1 at least at a temperature in the temperature range described above. Also, in this way, the unit resistance value ratio R3/R1 can be less than 1 at least at a temperature in the temperature range described above, and the precision of detection of the NOx concentration can be inhibited from decreasing. The volume resistivity ratio $\rho 3/\rho 1$ at least at a temperature in the temperature range described above is preferably 0.8 or less, more preferably 0.7 or less, further preferably 0.65 or less. The volume resistivity ratio $\rho 3/\rho 1$ may be 0.5 or more. For example, when the proportion of precious metal (a conductor) that is contained in the measurement chamber overlapping portion in the heat generation portion 76 is higher than that of the pump chamber overlapping portion, the volume resistivity $\rho 3$ can be less than the volume resistivity $\rho 1$. The values of the volume resistivity $\rho 1$ and $\rho 3$ are average values of those of the pump chamber overlapping portion and the measurement chamber overlapping portion as in the unit resistance values R1 and R3.

According to the embodiment described above, the unit resistance value R3/R1 is less than 1 but this is not a limitation. For example, in FIG. 2, the width of the second bend portion 77b may be equal to the widths of the first inner linear portion 79a and the second inner linear portion 79b, and the unit resistance value R3/R1 may be 1. Also, in this case, when "X1≥⅓×Wp" and "X2≥0.4Wp" are satisfied, a stress that is applied to the vicinity of the internal cavities of the sensor element 101 can be reduced when the heat generation portion 76 generates heat.

According to the embodiment described above, the heat generation portion 76 is bilaterally symmetric, and the central axis of the heat generation portion 76 in the left-right direction, the central axis of the main pump chamber projection region Ap in the left-right direction, the central axis of the auxiliary pump chamber projection region Aq in the left-right direction, and the central axis of the measurement chamber projection region Am in the left-right direction match each other, but this is not a limitation. For example, the heat generation portion 76 may be bilaterally asymmetric, or any one of the central axes described above may be away from the other central axes. Also, in this case, at least a part of the first inner linear portion 79a and a part of the second inner linear portion 79b overlap the main pump chamber projection region Ap, at least a part of the first inner linear portion 79a and a part of the second inner linear portion 79b overlap the auxiliary pump chamber projection region Aq, and "X1≥⅓×Wp" and "X2≥0.4Wp" are satisfied.

According to the embodiment described above, the shape of the main pump chamber projection region Ap, that is, the shape of the first internal cavity 20 in a top view is a rectangular shape, and the width of the main pump chamber projection region Ap in the transverse direction is constant (equal to the width Wp) as illustrated in FIG. 2, but this is not a limitation. For example, the width of the main pump chamber projection region Ap in the transverse direction may not be constant, for example, such that a portion of the main pump chamber projection region Ap has a width in the transverse direction less than that of another portion. In this case, the width Wp is the maximum width of the main pump chamber projection region Ap in the transverse direction. The same is true for the width Wq of the auxiliary pump chamber projection region Aq and the width Wm of the measurement chamber projection region Am.

EXAMPLES

Specific examples of making the sensor element will be described below. Experimental examples 3 to 6, 8, 9, and 10 correspond to examples according to the present invention, and experimental examples 1, 2, 7, and 11 correspond to comparative examples. The present invention is not limited to the examples below.

Experimental Example 1

A sensor element in an experimental example 1 was the same as the sensor element 101 illustrated in FIG. 1 and FIG. 2 except that "X1≥⅓×Wp" was not satisfied. As for the size of the sensor element in the experimental example 1, a length in the front-rear direction was 67.5 mm, a width in the left-right direction was 4.25 mm, and a thickness in the up-down direction was 1.45 mm. The widths of the first outer linear portion 78a and the second outer linear portion 78b were 0.28 mm. The widths of the first inner linear portion 79a and the second inner linear portion 79b were 0.33 mm. The width of a part of the second bend portion 77b other than parts that were connected to the first inner linear portion 79a and the second inner linear portion 79b was 0.53 mm. The width Wp of the main pump chamber projection region Ap was 2 mm. The width Wq of the auxiliary pump chamber projection region Aq was 1.6 mm. The width Wm of the measurement chamber projection region Am was 1.2 mm. The length of the measurement-object gas flow section was 8.3 mm. The distance X1 was 0.26 mm (equal to 0.13 Wp), and the distance X2 was 0.86 mm (equal to 0.43 Wp). For this reason, in the experimental example 1, "X2 0.4Wp" was satisfied, but "X1≥⅓×Wp" was not satisfied.

Experimental Examples 2 and 3

A sensor element in an experimental example 2 was the same as that in the experimental example 1 except that the distance X1 was 0.46 mm (equal to 0.23Wp). A sensor element in an experimental example 3 was the same as that in the experimental example 1 except that the distance X1 was 0.67 mm (equal to ⅓×Wp).

Experimental Example 4

As for a sensor element in an experimental example 4, the pattern of the heater 72 had a shape illustrated in FIG. 3. In the experimental example 4, the distance X1 and the distance X2 were 0.86 mm (equal to 0.43 Wp). The other dimensions were equal to those in the experimental example 1.

Experimental Examples 5 and 6

As for sensor elements in experimental examples 5 and 6, the pattern of the heater 72 had a shape illustrated in FIG. 4. In the experimental example 5, the distance X1 was 1.34 mm (equal to ⅔×Wp), and the distance X2 was 0.86 mm (equal to 0.43Wp). In the experimental example 6, the distance X1 was 1.67 mm (equal to 0.84Wp), and the distance X2 was 0.86 mm (equal to 0.43Wp). The other dimensions in the experimental examples 5 and 6 were equal to those in the experimental example 1.

Experimental Examples 7 to 9

As for sensor elements in experimental examples 7 to 9, the pattern of the heater 72 had the shape illustrated in FIG. 3. In the experimental example 7, the distance X1 and the distance X2 were 0.67 mm (equal to ⅓×Wp). In the experimental example 8, the distance X1 and the distance X2 were 1.34 mm (equal to ⅔×Wp). In the experimental example 9, the distance X1 and the distance X2 were 0.8 mm (equal to 0.4Wp). The other dimensions in the experimental examples 7 to 9 were equal to those in the experimental example 1.

[Evaluation of Stress]

As for each of the sensor elements in the experimental examples 1 to 9, the stress of each internal cavity applied to the sensor element and the stress of each outer circumferential portion when the heat generation portion 76 generated heat at 800° C. were investigated. The stress of each internal cavity was determined to be the maximum value of the stress applied to the vicinity of the first internal cavity 20, the second internal cavity 40, and the third internal cavity 61 of the sensor element, and the magnitude of the maximum value was used for evaluation at four steps of "Excellent (A)", "Good" (B), "Ok (C)", and "Failure (F)". The stress of each outer circumferential portion was determined to be the maximum value of the stress applied to the lower surface of the sensor element, and the magnitude of the maximum value was used for evaluation at the four steps of "Excellent (A)", "Good" (B), "Ok (C)", and "Failure (F)". Among these for the evaluation, "Excellent (A)" represented that the maximum value of the stress was smallest, and "Failure (F)" represented that the maximum value of the stress was largest.

Figure 5:
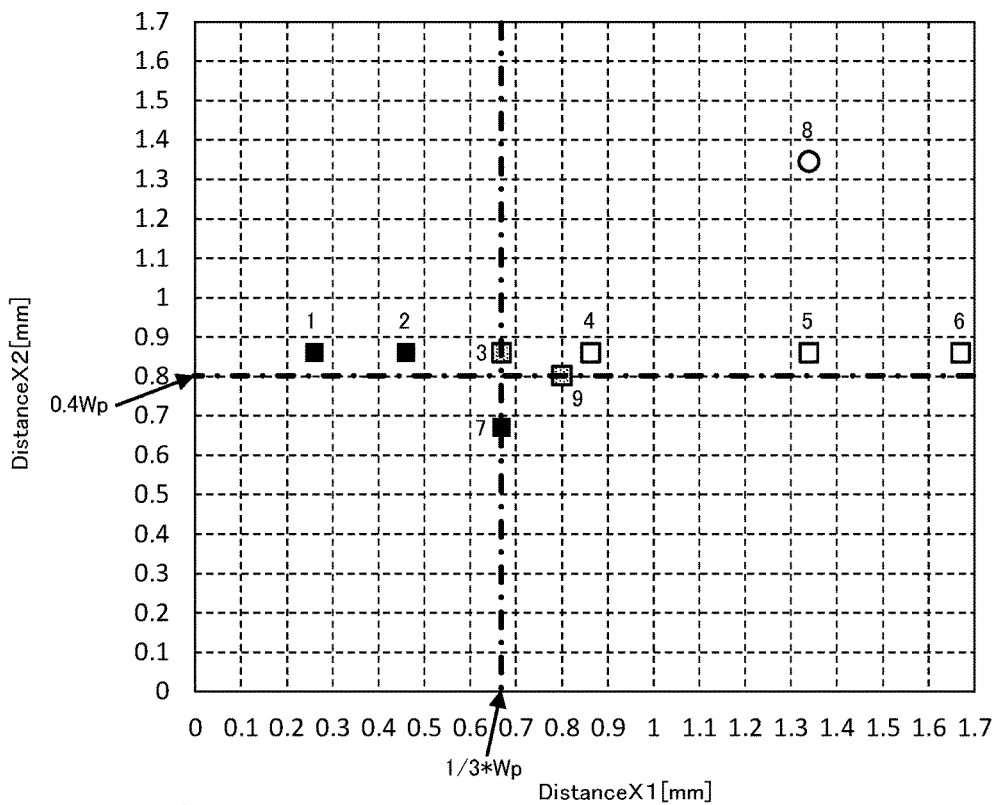
FIG. 5 is a graph in which distances X1 and X2 and the result of evaluation of a stress to each internal cavity in experimental examples 1 to 9 are plotted.
Figure 6:
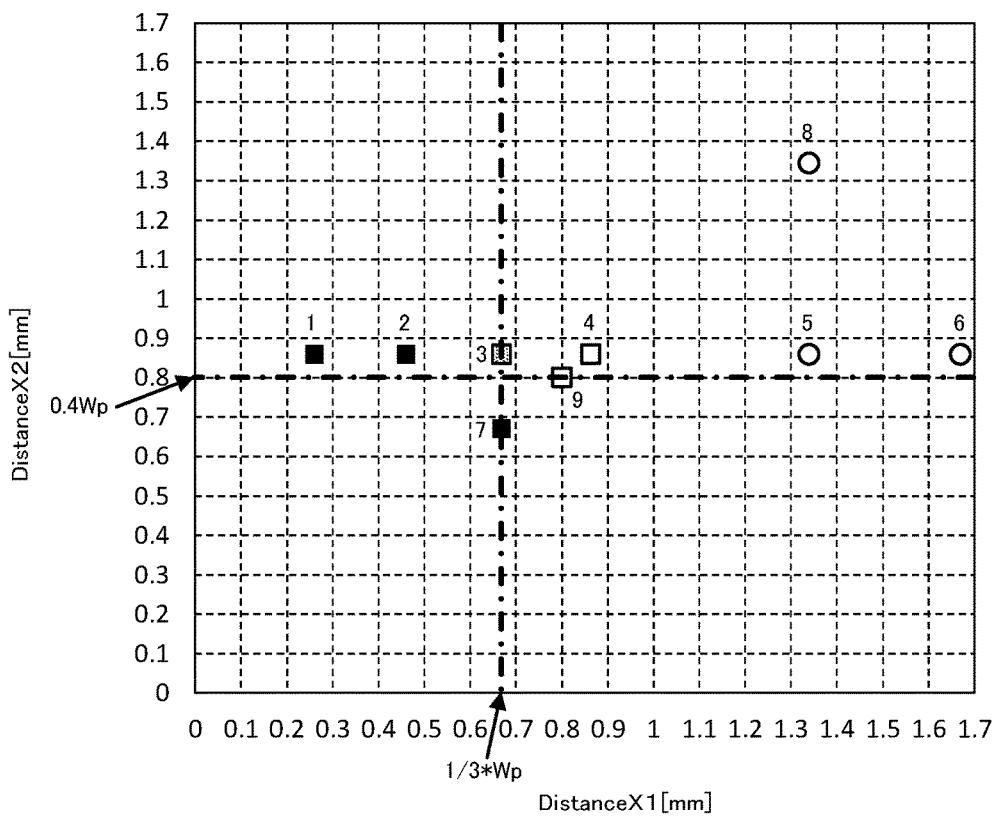
FIG. 6 is a graph in which the distances X1 and X2 and the result of evaluation of a stress to each outer circumferential portion in the experimental examples 1 to 9 are plotted.

The distances X1 and X2, the result of the evaluation of the stress of each internal cavity, and the result of the evaluation of the stress of each outer circumferential portion in the experimental examples 1 to 9 are illustrated in Table 1, FIG. 5, and FIG. 6. FIG. 5 illustrates the result of the evaluation of the stress of each internal cavity. FIG. 6 illustrates the result of the evaluation of the stress of each outer circumferential portion. Numerals 1 to 9 in FIG. 5 and FIG. 6 represent the number of each experimental example. As for the result of the evaluation of the stress, "Excellent (A)" is illustrated by a circle, "Good (B)" is illustrated by a whitewashed square, "Ok (C)" is illustrated by a hatched square, and "Failure (F)" is illustrated by a black square.

TABLE 1

| Experimental examples | X1[mm] | X2[mm] | Evaluation of a stress to each internal cavity | Evaluation of a stress to each outer circumferential portion |
|---|---|---|---|---|
| 1 | 0.26 (=0.13Wp) | 0.86 (=0.43Wp) | F | F |
| 2 | 0.46 (=0.23Wp) | 0.86 (=0.43Wp) | F | F |
| 3 | 0.67 (=⅓ * Wp) | 0.86 (=0.43Wp) | C | C |
| 4 | 0.86 (=0.43Wp) | 0.86 (=0.43Wp) | B | B |
| 5 | 1.34 (=⅔ * Wp) | 0.86 (=0.43Wp) | B | A |
| 6 | 1.67 (=0.84Wp) | 0.86 (=0.43Wp) | B | A |
| 7 | 0.67 (=⅓ * Wp) | 0.67 (=⅓ * Wp) | F | F |
| 8 | 1.34 (=⅔ * Wp) | 1.34 (=⅔ * Wp) | A | A |
| 9 | 0.8 (=0.4Wp) | 0.8 (=0.4Wp) | C | B |

As seen from Table 1 and FIG. 5, in the experimental examples 1 and 2 in which the former of "X1≥⅓×Wp" and "X2≥0.4Wp" was not satisfied and the experimental example 7 in which the latter was not satisfied, the result of the evaluation of the stress of each internal cavity was "Failure (F)". In contrast, in the experimental examples 3 to 6, 8, and 9 in which "X1≥⅓×Wp" and "X2≥0.4Wp" were satisfied, the result of the evaluation of the stress of each internal cavity was "Ok(C) or better. It is confirmed from these results that when "X1≥⅓×Wp" and "X2≥0.4Wp" are satisfied, the stress of each internal cavity can be reduced. In the experimental examples 4 to 6, and 8 in which "X1>0.4Wp" was satisfied, the result of the evaluation of the stress of each internal cavity was "Good (B)" or better. As seen from FIG. 5, it is confirmed that there is a tendency that the evaluation of the stress of each internal cavity is improved as the distances X1 and X2 increase, that is, in the experimental example plotted on the upper right in FIG. 5.

As for the result of the stress of each outer circumferential portion, the same tendency as that of the result of the stress of each internal cavity is confirmed. Specifically, as seen from Table 1 and FIG. 6, in the experimental examples 1 and 2 in which the former of "X1≥⅓×Wp" and "X2≥0.4Wp" was not satisfied and in the experimental example 7 in which the latter was not satisfied, the result of the stress of each outer circumferential portion was "Failure (F)". In contrast, in the experimental examples 3 to 6, 8, and 9 in which "X1≥⅓×Wp" and "X2≥0.4Wp" were satisfied, the result of the stress of each outer circumferential portion was "Ok(C)" or better. It is confirmed from these results that when "X1≥⅓×Wp" and "X2≥0.4Wp" are satisfied, the stress of each outer circumferential portion can be reduced. As seen from FIG. 6, it is confirmed that there is a tendency that the evaluation of the stress of each outer circumferential portion is improved as the distances X1 and X2 increase, that is, in the experimental example plotted on the upper right in FIG. 6.

Experimental Example 10

As for a sensor element in an experimental example 10, the pattern of the heater 72 had the shape illustrated in FIG. 3. In the experimental example 10, the distance X1 and the distance X2 were 0.86 mm (equal to 0.43Wp) as in the experimental example 4. The other dimensions were equal to those in the experimental example 1. For this reason, in the experimental example 10, "X1≥⅓×Wp" and "X2 0.4Wp" were satisfied.

Experimental Example 11

Figure 7:
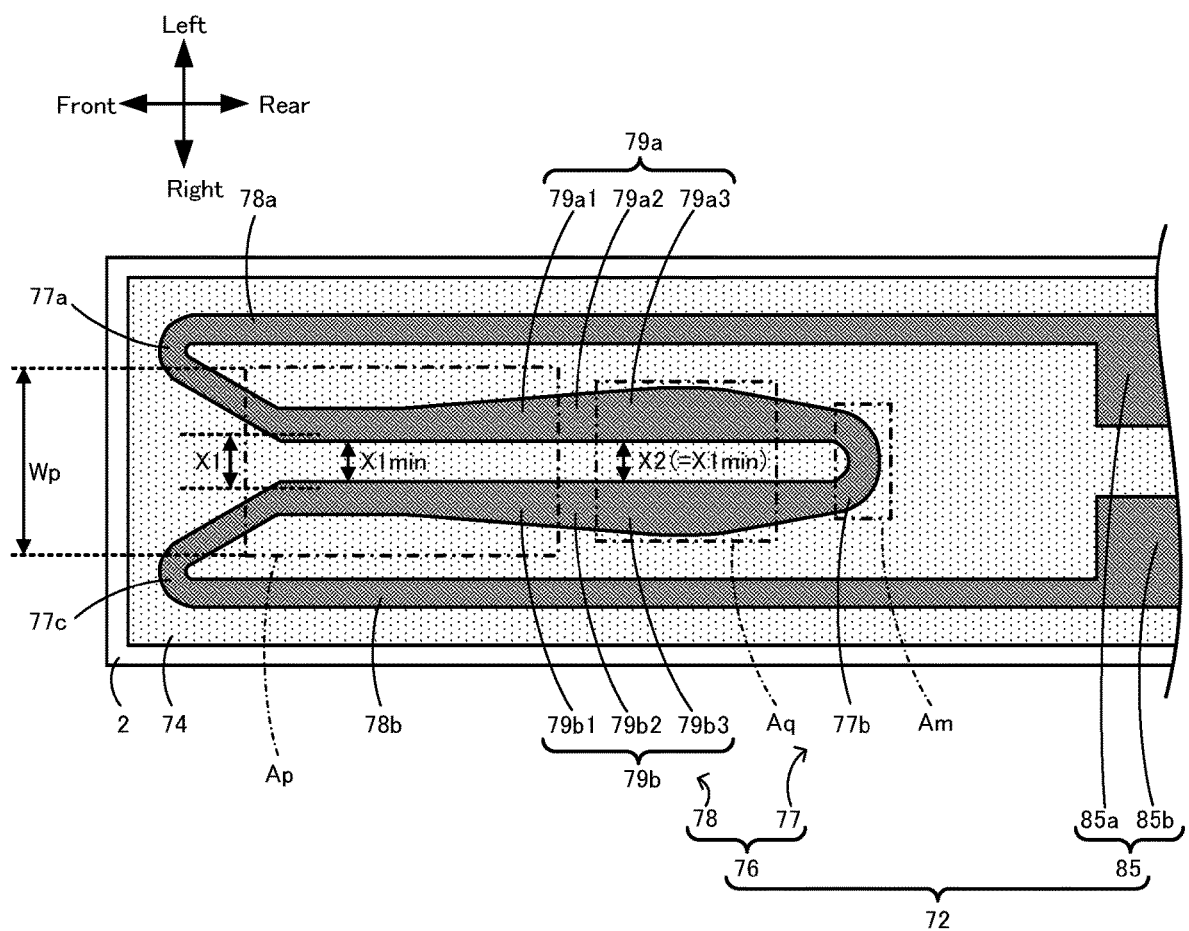
FIG. 7 illustrates the heater 72 in an experimental example 11.

As for a sensor element in an experimental example 11, the pattern of the heater 72 had a shape illustrated in FIG. 7. In the experimental example 11, as illustrated in FIG. 7, the widths of a part of the first inner linear portion 79a and a part of the second inner linear portion 79b were increased, and the widths of parts that overlapped the auxiliary pump chamber projection region Aq were greatest. The front side part 79a1 of the first inner linear portion 79a included a part the length direction of which inclined with respect to the longitudinal direction (the front-rear direction) of the sensor element and a part the length direction of which is parallel with the longitudinal direction (front-rear direction). The same was true for the front side part 79b1 of the second inner linear portion 79b. The distance in the left-right direction between the part inclining with respect to the front-rear direction in the front side part 79a1 and the part inclining with respect to the front-rear direction in the front side part 79b1 increased as the positions thereof were closer to the front end of the sensor element. The distance in the left-right direction between the front side part 79a1 and the front side part 79b1 was not constant, and the distance in the left-right direction between a part parallel with the front-rear direction in the front side part 79a1 and a part parallel with the front-rear direction in the front side part 79b1 was equal to the minimum distance X1 min between the front side part 79a1 and the front side part 79b1 in the left-right direction. The minimum distance X1 min was 0.47 mm. The distance X1 was the average value of the distance in the transverse direction (the left-right direction) between a part of the first inner linear portion 79a and a part of the second inner linear portion 79b that overlapped the main pump chamber projection region Ap. The distance X1 was longer than the minimum distance X1 min and was 0.49 mm. The distance in the left-right direction between the rear side part 79a3 and the rear side part 79b3 was constant and was equal to the minimum distance X1 min. Accordingly, the distance X2 was equal to the minimum distance X1 min and was 0.47 mm. The width of the second bend portion 77b was 0.33 mm. The other dimensions were equal to those in the experimental example 1. The width Wp of the main pump chamber projection region Ap was 2 mm. For this reason, in the experimental example 11, neither "X1≥⅓×Wp" nor "X2≥0.4Wp" were satisfied.

[Evaluation of Crack Incidence]

As for the sensor elements in the experimental examples 10 and 11, a crack incidence when the temperature of the heat generation portion 76 was increased was measured. Specifically, ten of the sensor elements in the experimental example 10 and ten of the sensor elements in the experimental example 11 were first prepared. Subsequently, a constant voltage was applied to the heater 72 such that the temperature of the heater 72 of each sensor element reached a target temperature (800° C.), and the temperature of the heat generation portion 76 was increased. Subsequently, whether each sensor element cracked was checked. This condition of the increase in the temperature is a condition in which the temperature of the heater 72 is increased to the target temperature in a shorter time than that when the sensor element is usually used. In this condition, the sensor element cracked to a certain extent. In the experimental example 10, four sensor elements of the ten sensor elements cracked, and the crack incidence was 40%. In the experimental example 11, all of the ten sensor elements cracked, and the crack incidence was 100%. It was confirmed from these results that the crack incidence in the experimental example 10 in which "X1≥⅓×Wp" and "X2≥0.4Wp" were satisfied was lower than that in the experimental example 11 in which neither "X1≥⅓×Wp" nor "X2≥0.4Wp" was satisfied. It is considered that in the experimental example 10, the crack incidence was low because "X1≥⅓×Wp" and "X2≥0.4Wp" were satisfied, and the stress of each internal cavity was reduced.

What is claimed is:

1. A sensor element comprising:
   an element body that includes an oxygen-ion-conductive solid electrolyte layer, that contains a measurement-object gas flow section into which measurement-object gas is introduced and through which the measurement-object gas flows, that has a longitudinal direction, a transverse direction, and a thickness direction perpendicular to the longitudinal direction and the transverse direction, and that has a plate shape;
   a main pump cell that adjusts an oxygen concentration of a main pump chamber in the measurement-object gas flow section;
   an auxiliary pump cell that adjusts an oxygen concentration of an auxiliary pump chamber that is formed downstream of the main pump chamber in the measurement-object gas flow section;
   a measurement pump cell that adjusts an oxygen concentration of a measurement chamber that is formed downstream of the auxiliary pump chamber in the measurement-object gas flow section; and
   a heating element that heats the element body,
   wherein the heating element includes
   a first outer linear portion and a second outer linear portion that are arranged in the transverse direction and that have a length direction parallel with the longitudinal direction,
   a first inner linear portion and a second inner linear portion that are disposed between the first outer linear portion and the second outer linear portion in the transverse direction and that have a length direction parallel with the longitudinal direction,
   a first bend portion that connects the first outer linear portion and the first inner linear portion to each other at a first end in the longitudinal direction,
   a second bend portion that connects the first inner linear portion and the second inner linear portion to each other at a second end in the longitudinal direction, and
   a third bend portion that connects the second inner linear portion and the second outer linear portion to each other at the first end in the longitudinal direction,
   wherein at least a part of the first inner linear portion and a part of the second inner linear portion overlap a main pump chamber projection region on which the main pump chamber is projected toward the heating element in the thickness direction,
   wherein at least a part of the first inner linear portion and a part of the second inner linear portion overlap an auxiliary pump chamber projection region on which the auxiliary pump chamber is projected toward the heating element in the thickness direction,
   wherein a distance X1 in the transverse direction between the part of the first inner linear portion and the part of the second inner linear portion that overlap the main pump chamber projection region is equal to or more than ⅓ of a width Wp of the main pump chamber projection region in the transverse direction, and wherein a distance X2 in the transverse direction between the part of the first inner linear portion and the part of the second inner linear portion that overlap the auxiliary pump chamber projection region is equal to or more than 0.4 times the width Wp.

2. The sensor element according to claim 1, wherein the distance X1 is more than 0.4 times the width Wp.

3. The sensor element according to claim 1, wherein a unit resistance value ratio R3/R1 is less than 1 at least at a temperature in a temperature range of no less than 700° C. and no more than 900° C., where a unit resistance value R1 [$\mu\Omega$/mm] is a resistance value per unit length of a pump chamber overlapping portion that overlaps a pump chamber projection region on which the main pump chamber and the auxiliary pump chamber are projected toward the heating element in the thickness direction in the heating element, and a unit resistance value R3 [$\mu\Omega$/mm] is a resistance value per unit length of a measurement chamber overlapping portion that overlaps a measurement chamber projection region on which the measurement chamber is projected toward the heating element in the thickness direction in the heating element.

4. A gas sensor comprising:

the sensor element according to claim 1.

* * * * *